United States Patent
Foreman et al.

(10) Patent No.: US 6,284,235 B1
(45) Date of Patent: Sep. 4, 2001

(54) BIOADHESIVE COMPOSITION

(75) Inventors: Paul B. Foreman, Somerville; Paul Richardson, Plainsboro; John Tsai, Belle Mead, all of NJ (US); Jean Paul Remon, Melle (BE); Jody Voorspoels, Reningelst (BE); Dieter Ameye, Waregem (BE); Catherine Callens, Ploegsteert (BE)

(73) Assignee: National Starch and Chemical Company Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/502,585

(22) Filed: Feb. 11, 2000

(51) Int. Cl.$^7$ ..................................... A61K 31/74
(52) U.S. Cl. .................. 424/78.08; 424/486; 424/488; 514/778; 514/781; 514/782; 514/783
(58) Field of Search ................................ 424/78.08, 486, 424/488; 514/778, 781, 782, 783

(56) References Cited

U.S. PATENT DOCUMENTS

| | | | |
|---|---|---|---|
| 4,915,948 | * | 4/1990 | Gallopo et al. ................ 424/435 |
| 5,643,603 | * | 7/1997 | Bottenberg et al. ............ 424/488 |
| 5,895,804 | | 4/1999 | Lee et al. . |
| 5,968,500 | * | 10/1999 | Robinson ..................... 424/78.08 |

FOREIGN PATENT DOCUMENTS

| | | | |
|---|---|---|---|
| 0 410 696 A1 | * | 1/1991 | (EP) .................. A61K/9/70 |
| 0 911 361 A1 | | 4/1999 | (EP) . |
| WO 98/22097 A2 | * | 5/1998 | (WO) ................. A61K/9/70 |
| WO 00/47644 | | 8/2000 | (WO) . |

OTHER PUBLICATIONS

Junginger, H.E. "Bioadhesive Polymer Systems for Peptide Delivery", Acta Pharmaceutica Technologica, DE, Wissenschaftliche Verlagsgesellschaft, Stuttgart, Sep. 1, 1990, vol. 36, No. 3, pp. 115–118.

* cited by examiner

*Primary Examiner*—Thurman K. Page
*Assistant Examiner*—Liliana Di Nola-Baron
(74) *Attorney, Agent, or Firm*—Cynthia L. Foulke

(57) ABSTRACT

This invention relates to a method of producing a bioadhesive composition comprising the steps of preparing a solution of a solvent and a polymer mixture wherein the polymer mixture comprises at least one natural or synthetic polycarboxylated polymer and at least one polysaccharide; drying the solution to form a solid; and heat treating the solid to effect cross-linking and to form the bioadhesive composition.

10 Claims, 5 Drawing Sheets

BIOADHESIVE COMPOSITION

FIELD OF THE INVENTION

This invention relates to a method for the preparation and use of a bioadhesive composition.

BACKGROUND OF THE INVENTION

Carboxylated polymers, such as poly(acrylic) acid, are known to be effective as bioadhesive compositions, but their use is limited owing to problems associated with mucosa irritation. To overcome these problems, it is known to blend these polymers with other materials such as starch (as described in U.S. Pat. No. 5,643,603 (Janssen Pharmaceuticals)).

Known bioadhesive compositions are described in WO 98/22097 (Bio Advances); EP 410,696 (E. R. Squibb); U.S. Pat. No. 5,643,603 (Janssen Pharmaceuticals); and U.S. Pat. No. 4,915,948 (Warner-Lambert).

WO 98/22097 refers to compositions of poly(acrylic) acid and a polar polymer or monomer produced under conditions that ensure hydrogen bonding interactions, rather than cross-linking, occur.

EP 410,696 discloses a mucoadhesive delivery system comprising poly(acrylic) acid crosslinked with 1 percent to 20 percent by weight of a polyhydroxy compound and a therapeutically effective amount of a drug. This invention is concerned with the use of low molecular weight polyhydroxy compounds.

U.S. Pat. No. 5,643,603 describes a bioadhesive carrier composition which is a tablet formulated from pregelatinized starch, synthetic polymer such as poly(acrylic) acid and a drug. The pregelatinized starch is used as a substitute adhesive allowing for lower loading of poly(acrylic) acid to reduce corresponding irritation effects.

U.S. Pat. No. 4,915,948 refers to a tablet with bioadhesive properties prepared from a blend of xanthan gum and/or a pectin combined with a solid polyol. The blend is prepared without any form of heating.

Prior art methods of crosslinking polycarboxylated polymers with polysaccharides include the method described in U.S. Pat. No. 5,895,804 (National Starch and Chemical) wherein polysaccharide and polycarboxylated polymer are combined under conditions effective to induce crosslinking of the polycarboxylated polymer.

None of the above patents or references provide a method of preparing bioadhesive compositions having the high loading of poly(acrylic) acid and corresponding adhesion and low irritation properties described in this invention.

SUMMARY OF THE INVENTION

The present invention relates to a method of producing a bioadhesive composition which comprises the steps of preparing a solution of at least one solvent and a polymer mixture wherein the polymer mixture comprises from about 10 percent by weight to about 90 percent by weight of at least one natural or synthetic polycarboxylated polymer and about 10 percent by weight to about 90 percent by weight of at least one polysaccharide; drying the solution to form a solid; and heat treating the solid at a temperature from about 60° C. to about 200° C. to effect cross-linking and to form the bioadhesive composition.

Any suitable aqueous or organic solvent may be used in this invention. The preferred solvent is water.

Solid, as used herein, is intended to mean a material having less than about 20 percent by weight of solvent present, and includes powders.

Solution, as used herein, is intended to mean a partial or total solubilization.

Neutralization, as used herein, may be partial or total. Such neutralization may be carried out by, but is not limited to, the use of ammonia, or any metal cations of the Group I or Group II elements of the Periodic Table.

The drying and heat treating steps may be carried out together as a one step process or individually as a two step process.

The chemistry of the natural or synthetic polycarboxylated polymer may be selected by one skilled in the art to control the degree and location of ester crosslinking.

The bioadhesive compositions produced by the method of this invention do not contain residual monomer or chemical residue, and therefore do not require a post-washing step. As the natural or synthetic polycarboxylated polymer is cross-linked to the polysaccharide backbone higher levels of natural or synthetic polycarboxylated polymer, such as poly (acrylic) acid, may be incorporated into the composition to provide good adhesion properties and low mucosa irritation.

By bioadhesive composition is meant a component that provides bioadhesive properties to a bioadhesive system in which it is included rather than, for instance, an excipient in a bioadhesive system. Bioadhesive properties mean that adhesive properties are developed on contact with animal or human mucosa, skin or body tissue or vegetable or plant tissues wherein some water or an aqueous solution is present. Typical, but non-limiting, examples of types of bioadhesives include intestinal, nasal, buccal, sub-lingual, vaginal and ocular bioadhesives. Bioadhesion compositions may be neutralized by known means.

Bioadhesion, as used herein, is intended to mean the ability of a material (synthetic or biological) to adhere to biological tissue. Bioadhesion stages can be summarized as follows. First an intimate contact must exist between the bioadhesive and the receptor tissue. Such contact results either from a good wetting of the bioadhesion surface or from the swelling of the bioadhesive. When contact is established, the penetration of the bioadhesive into the crevice of the tissue surface then takes place, or there is interpenetration of bioadhesive chains with those of the mucus, and there is formation of weak chemical bonds between entangled chains. A general description of bioadhesion may be found in the publication Bioadhesive Drug Delivery Systems, 1999, pp. 1–10, Published by Marcel Dekker.

Controlled release, as used herein, is intended to mean a method and composition for making an active ingredient available to the biological system of a host. Controlled-release includes the use of instantaneous release, delayed release, and sustained release. "Instantaneous release" refers to immediate release to the biosystem of the host. "Delayed release" means the active ingredient is not made available to the host until some time delay after administration. "Sustained Release" generally refers to release of active ingredient whereby the level of active ingredient available to the host is maintained at some level over a period of time. The method of effecting each type of release can be varied. For example, the active-ingredient can be associated physically and/or chemically with a surfactant, a chelating agent, etc. Alternatively, the active ingredient can be masked by a coating, a laminate, etc. Regardless of the method of providing the desired release pattern, the present invention contemplates delivery of a controlled-release system that utilizes one or more of the "release" methods and compositions. Moreover, the present invention can be an element of the release method and/or composition, especially with respect to sustained release systems.

The bioadhesive composition of the present invention may take up and controllably release active components such as drugs. Active components may be added using any of the known methods described in the prior art, and such addition may be carried out during and/or after the production of the bioadhesive composition. Typical active components may include, but are not limited to, a therapeutic substance or a pharmaceutically active agent such as a drug, a non-therapeutic substance such as a cosmetic substance, a local or general anesthetic or pain killer, or an opiate, a vaccine, an antigen, a microorganism, a sterilizing substance, a contraceptive composition, a protein or peptide such as insulin, an insecticide, a herbicide, a hormone such as a growth hormone or a seed germination hormone, a steroid, a toxin, or a marker substance. A non-limiting list of possible active components includes hydrochlorothiazide, acetazolamide, acetylsalicyclic acid, allopurinol, alprenolol, amiloride, antiarrhythmics, antibiotics, antidiabetics, antiepileptics, anticoagulants, antimycotics, atenolol, bendroflumethiazide, benzbromarone, benzthiazide, betamethasone, bronchodilators, buphenine, bupranolol, chemotherapeutics, chlordiazepoxide, chlorquine, chloro thiazide, chlorpromazine, chlortalidone, clenbuterol, clomipramine, clonidine, co-dergocrine, cortisone, dexamethasone, dextropropoxyphene, diazepam, diazoxide, diclofenac, diclofenamide, digitalisglycoside, dihydralazine, dihydroergotamine, diltiazem, iron salt, ergotamine, ethacrynic acid, ethinylestradiol, ethoxzolamide, fenoterol, fludrocortisone, fluphenazine, fluorosemide, gallopamil, guanethidine, hormones, hydrochlorothiazide, hydrocortisone, hydroflumethiazide, immunosuppresives, ibuprofen, imipramine, indomethacine, coronartherapeutics, levodopa, lithium salt, magnesium salt, medroxyprogesteron acetate, manadione, methaqualone, 8-methoxypsoralen, methylclothiazide, methyldopa, methylprednisolone, methyltestosterone, methylthiouracil, methylxanthine, metipranolol, molsidomine, morphine, naproxen, nicergline, nifedipine, norfenefrine, oxyphenbutazone, papaverine, parmathasone, pentobarbital, perphenazine, phenobarbital, phenylbutazone, phytomenadione, pirenzepine, polythiazide, prazosine, prednisolone, prednisone, probenecid, propranolol, propylthiouracil, rescinnamine, reserpine, secbutabarbital, secobarbital, spironolactone, sulfasalazine, sulfonamide, testosterone, thioridazine, triamcinolon, triamteren, trichloromethiazide, trifluoperazine, trifluopromazine, tuberculostatic, verapamil, virustatics, zytostatics, bromocriptine, bromopride, carbidopa, carbocromen, quinine, chlorprothixene, cimetidine, clofibrat, cyclizine, desipramine, disulfiram, domperidone, doxepine, fenbufen, flufenamine acid, flunarizine, gemfibrocil, haloperidol, ketoprofen, labetalol, lorazepam, mefenamine acid, melperone, metoclopramide, nortriptyline, noscapine, oxprenolol, oxymetholone, pentazocine, pethidine, stanozolol, sulindac, sulpiride, tiotixen.

The term "bioadhesive system" as used herein includes any system or product comprising the bioadhesive composition of this invention.

BRIEF DESCRIPTION OF THE DRAWING FIGURES

DETAILED DESCRIPTION OF THE INVENTION

Figure 1:
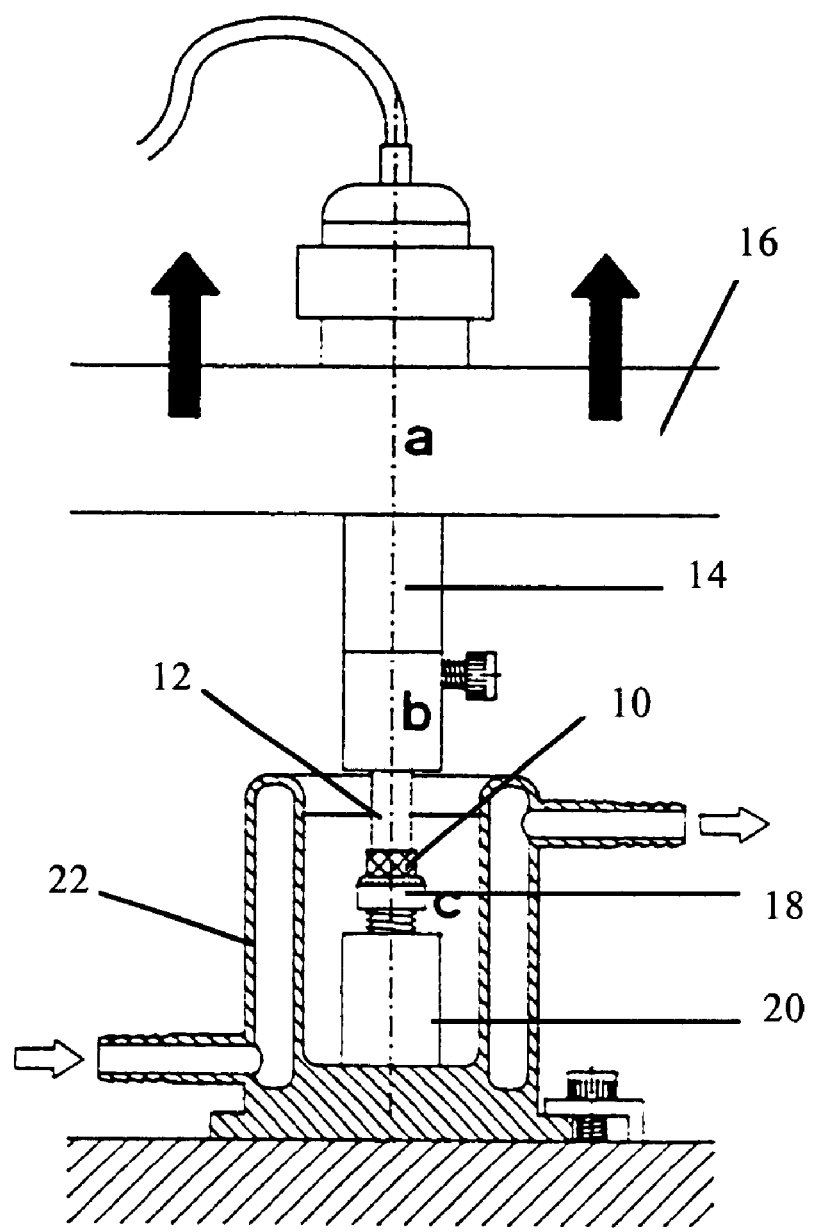
FIG. 1 is a schematic of test equipment for measuring bioadhesion.

This invention provides compositions having improved bioadhesion properties, where such compositions are prepared from a solution of a natural or synthetic polycarboxylated polymer and a polysaccharide molecule by means of drying the solution to form a solid and heat treating the solid to induce cross-linking.

The bioadhesive compositions produced by the method of this invention do not contain residual monomer or chemical residue, and therefore do not require a post-washing step. As natural or synthetic polycarboxylated polymer is cross-linked to the polysaccharide backbone higher levels of the natural or synthetic polycarboxylated polymer, such as poly (acrylic) acid, may be incorporated into the composition to provide good adhesion properties and low mucosa irritation properties. The bioadhesive compositions may be neutralized.

Preparation of the bioadhesive composition of this invention may be accomplished by preparing a solution by means of charging at least one solvent, preferably water, and a polymer mixture comprising about 10 percent by weight to about 90 percent by weight of polysaccharide and about 10 percent by weight to about 90 percent by weight of natural or synthetic polycarboxylated polymer into a reaction vessel. In order to partially or totally solubilize the mixture, the solution may be heated and stirred for a short period.

The mixture is then dried by conventional means, including, but not limited to, spray drying, freeze drying, air drying, drum drying and extrusion, to provide a solid. The solid produced during the drying stage preferably has a moisture content of less than about 20 percent by weight. The resultant solid is then heat treated at a temperature of about 60° C. to about 200° C., preferably from about 80° C. to about 120° C., by a suitable method to induce cross-linking. Suitable methods of heat treatment include, but are not limited to, oven heat treatment, drum drying, extrusion, fluidized bed and IR radiation. The time required to complete cross-linking is determined by the means of heating and by the composition of the solid. For those skilled in the art, comparable cross-linking may be achieved by lowering the heat treatment temperature and increasing heat treatment time and visa versa. As determined by one skilled in the art, the overall time may vary from about 1 second to 6 hours dependent upon the degree of cross-linking required. Less heat treatment is generally required for mixtures containing higher levels of natural or synthetic polycarboxylated polymer. The drying and heat treating process may be carried out in one step or two steps.

The natural or synthetic polycarboxylated polymers of this invention may be modified or unmodified and have a weight average molecular weight of at least 1,000 Daltons. Such modifications may include, but are not limited to cross-linking, neutralization, hydrolysis, enzyme treatment and partial esterification.

Exemplary synthetic polycarboxylated polymers which may be used in the present invention include without limitation poly(acrylic acid) and carboxylic-acid-functionalized polyesters. Also included are polymers containing carboxyl groups and prepared from monomers such as, vinyl acetate (VA), (meth)acrylic acid (M)AA, the $C_1$ to $C_8$ alkyl esters of (meth)acrylic acid, maleic anhydride (MAnh), maleic acid, itaconic acid (IA), crotonic acid (CA), and beta-carboxy ethyl acrylate (BCEA). (Meth)acrylic is used herein to denote both acrylic and methacrylic acids and esters thereof. These examples are not limiting and the polysaccharides according to the present invention may be used in combination with virtually any natural or synthetic polycarboxylated polymer.

Natural polycarboxylated polymers include, but are not limited to xanthan, low methoxyl pectin, alginate, hyaluronic acid, polyaspartic acid, polyglutamic acid and pectic acid. The term "natural polycarboxylated polymers" also encompasses modified natural polycarboxylated polymers including, but not limited to, carboxymethylated starch, oxidized guar, oxidized starch and carboxymethylcellulose.

Typical synthetic polycarboxylated polymers of this invention include acrylic acid polymers crosslinked with allyl ethers of sucrose, pentaerythritol or divinyl glycol. Such polymers are available from B F Goodrich Specialty Chemicals, Cleveland, Ohio under the trade names CARBOPOL® and NOVEON®. Particularly suitable are the pharmaceutical grades CARBOPOL® 971P, CARBOPOL® 934P and CARBOPOL® 974P.

The amount of natural or synthetic polycarboxylated polymer may vary from about 10 percent to about 90 percent, preferably from about 25 percent to about 83 percent, by weight of the final bioadhesive composition of this invention.

The polysaccharides of the present invention are derived from natural products, including plant, animal and microbial sources. Examples of polysaccharides include starch, cellulose and gums such as galactomannans. Polysaccharide starches include maize or corn, waxy maize, potato, cassava, tapioca and wheat starch. Other starches include varieties of rice, waxy rice, pea, sago, oat, barley, rye, amaranth, sweet potato, and hybrid starches available from conventional plant breeding, e.g., hybrid high amylose starches having amylose content of 40 percent or more, such as high amylose corn starch. Also useful are genetically engineered starches such as high amylose potato and waxy potato starches.

The polysaccharides may be modified or derivatized, such as by etherification, esterification, acid hydrolysis, dextrinization, crosslinking, pregelatinization or enzyme treatment (e.g., with alpha-amylase, beta-amylase, pullulanase, isoamylase, or glucoamylase).

The preferred polysaccharide of the present invention has a weight average molecular weight of at least 10,000 Daltons.

Other materials known in the art may be added to the mixture of polysaccharide and the natural or synthetic polycarboxylated polymer as desired to aid in the efficiency of the cross-linking.

To determine the bioadhesive characteristics of a material, the following method was used.

The apparatus used for the determination of the ex vivo bioadhesion characteristics consisted of a tensile testing machine (type L1000R, Lloyd Instruments, Segenwordt, Fareham, UK), equipped with a 20 N load cell with an accuracy of less than 1 percent. The apparatus was connected to a computer.

Porcine gingiva were obtained from a slaughterhouse directly after slaughtering. They were rapidly frozen and stored in isotonic phosphate-buffered saline pH 7.4 (2.38 g $Na_2HPO_4.2H_2O$, 0.19 g $KH_2PO_4$ and 8.0 g NaCl made up to 1000 mL with demineralized water). Tablets of 100 mg of the material to be tested were directly compressed at a pressure of 1500 kg with the given polymers without any other excipient. An ecentric compression machine (Korsch, type EKO, Frankfurt, Germany) equipped with 7 mm flat punches was used. The test equipment for measuring bioadhesion is shown schematically in FIG. 1. The tablet 12 under test was attached to the upper aluminum support 14, connected to the superior cross-sectional bar 16 of the tensile tester with a cyanoacrylate glue. The porcine gingival tissue (±100 mm²) 10 was glued (mucosal side out) with the same adhesive to a Teflon support 18, which was connected to a PVC cylinder 20 situated at the bottom of a 150 mL thermostatted beaker 22 fixed on the base of a tensile tester. Next, 15 µL of isotonic phosphate buffer (pH 7.4) was spread evenly over the mucosa 10, and the crosspiece 16 (bearing the tablet 12) was lowered at a crosshead speed of 1 mm.min$^{-1}$. After initial contact, the thermostatted beaker 22 was filled with the buffer solution up to a total volume of 125 mL to act as a counterweight. The mucosa 10 and the tablet 12 were then pressed together with a force of 0.5 N for 5 min., after which the tablet 12 and the mucosa 10 were pulled apart at a constant extension rate of 5 mm.min$^{-1}$ until complete rupture of the tablet-mucosa bond was obtained.

Figure 2:
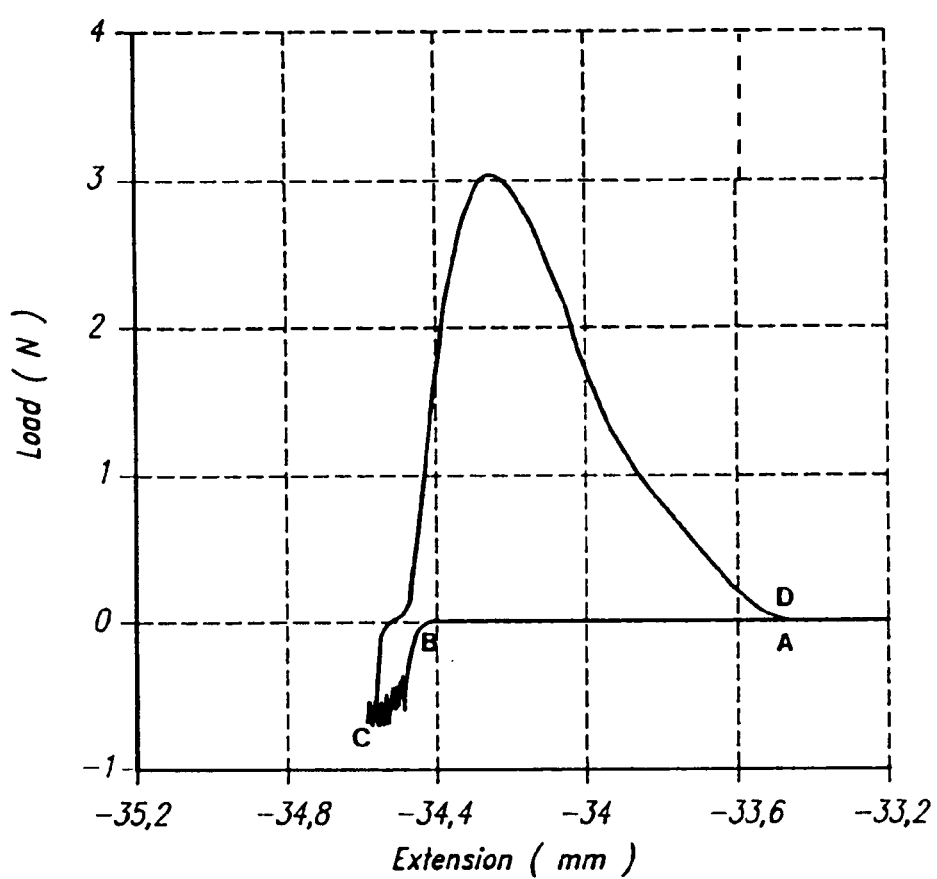
FIG. 2 is a force vs. extension diagram.

A force vs. extension diagram (FIG. 2) was constructed, and the maximal detachment force and the work of adhesion necessary to break the bond between tablet and mucosa were calculated. The work of adhesion is calculated from the area under the force/extension diagram.

EXAMPLES

As used in the following examples, Sample 1 and Comparative Sample 2 were prepared as follows:

250 g waxy corn starch (AMIOCA) was bath cooked (90° C. for 30 minutes) at 20 percent solids in water. This solution was mixed with 2.14 liters of a 35 wt percent solution of poly(acrylic acid) (a 35 wt. percent solution in water, having average mol. wt. ca. 250,000, available from Aldrich Chemical Company, Inc.) using a Baldor motor and stirrer paddle for 2 hours. The solution was then freeze dried using a Flexi-dry MP (FTS Systems) and vacuum pump. The dried solid was ground to a powder using a coffee mill.

Sample 1 was prepared by oven heat treatment of the powder at 120° C. for 15 minutes.

Comparative Sample 2 comprised the powder having not undergone heat treatment.

Example 1

Trypsin Inhibition

The trypsin inhibition capacity of Sample 1 and a "blank" containing no polymer were determined using a trypsin inhibition assay described by Lueβen et al. (Eur. J. Pharm. Sci. 4 (1996) pp. 117–128) that was optimized and validated as follows:

Trypsin (TPCK treated from bovine pancreas), N-α-benzoyl-L-arginine-ethylester (BAEE), N-α-benzoylarginine (BA) and 2-[N-morpholino]ethane-sulfonic acid (MES) were purchased from Sigma, Bornem, Belgium. All other chemicals used were at least of analytical grade.

The buffer system used in the trypsin inhibition study was a 50 mmol/l 2-[N-morpholino]ethane-sulfonic acid (MES)/KOH buffer, pH 6.7, containing 250 mmol/l mannitol.

HPLC analysis was performed with a HPLC system consisting of an isocratic HPLC pump (type L-7110, Merck-Hitachi, Darmstadt, Germany); an injector with a loop of 20 µl (Valco 6 channel injector; Valco Instruments Corporation, Houston, USA); a UV detector (type L-7400, Merck-Hitachi, Darmstadt, Germany); and a software interface (type D-7000, Merck-Hitachi, Darmstadt, Germany). Data were calculated with the software package 'HPLC System Manager' (Merck-Hitachi, Darmstadt, Germany). The column was a Lichrosorb 7 RP 18 column (100×3.0 mm) equipped with a RP precolumn (10×2 mm) (Chrompack, Antwerpen, Belgium). The mobile phase, used as an isocratic eluent, consisted of 86 percent (v/v) 10 mmol/l ammonium acetate buffer pH 4.2 with 10 mmol/l triethylamine and 14 percent (v/v) acetonitrile. The analysis was performed at room temperature.

Amounts of 20 mmol/l N-α-benzoyl-L-arginine-ethylester (BAEE), the model substrate for trypsin, were dissolved in the polymer preparation (Sample 1) dispersed in a 50 mmol/l MES/KOH buffer, pH 6.7, with 250 mmol/l mannitol. The pH of the test medium was 6.7 and was within the optimal activity range of trypsin, which is between pH 6 and 9. At time zero 30 Enzymatic Units trypsin/ml (enzymatic activity determined according the Enzymatic Assay of Trypsin used by Sigma, Bornem, Belgium) were added to the polymer preparation, after which the solution was incubated at 37° C. for 1 hour. 50 µl of sample was withdrawn at predetermined time intervals and diluted in 1.0 ml 0.1M HCL to stop the trypsin activity. The degradation of the substrate BAEE was studied by determining the formation of the metabolite N-α-benzoylarginine (BA) by HPLC with UV detection at 253 nm. The retention time of the metabolite peak was 1.3 min after injection of 20 µl at a flow rate of 0.75 ml/min. The degree of trypsin inhibition was expressed by the Inhibition Factor: IF=reaction rate$_{control}$/reaction rate$_{polymer}$. The IF is defined as the ratio of the reaction rate of the metabolite concentration time curve for the enzymatic reaction carried out without polymer (Blank) and with polymer, respectively. The reaction rate was calculated by linear regression analysis of the N-α-benzoylarginine (BA) concentration versus reaction time. The correlation coefficients of the linear progress functions during 1 hour of incubation time were >0.995. The optimised HPLC method was validated. The standard curves (n=6) were linear with correlation coefficients >0.999. For repeatability (i.e. all within the same day) n=6, and for reproducibility (i.e. on different days) n=6; therefore, coefficients of variation were <3 percent. The detection limit of the degradation product BA was 0.0003 mmol/l and the quantification limit 0.010 mmol/l.

Figure 3:
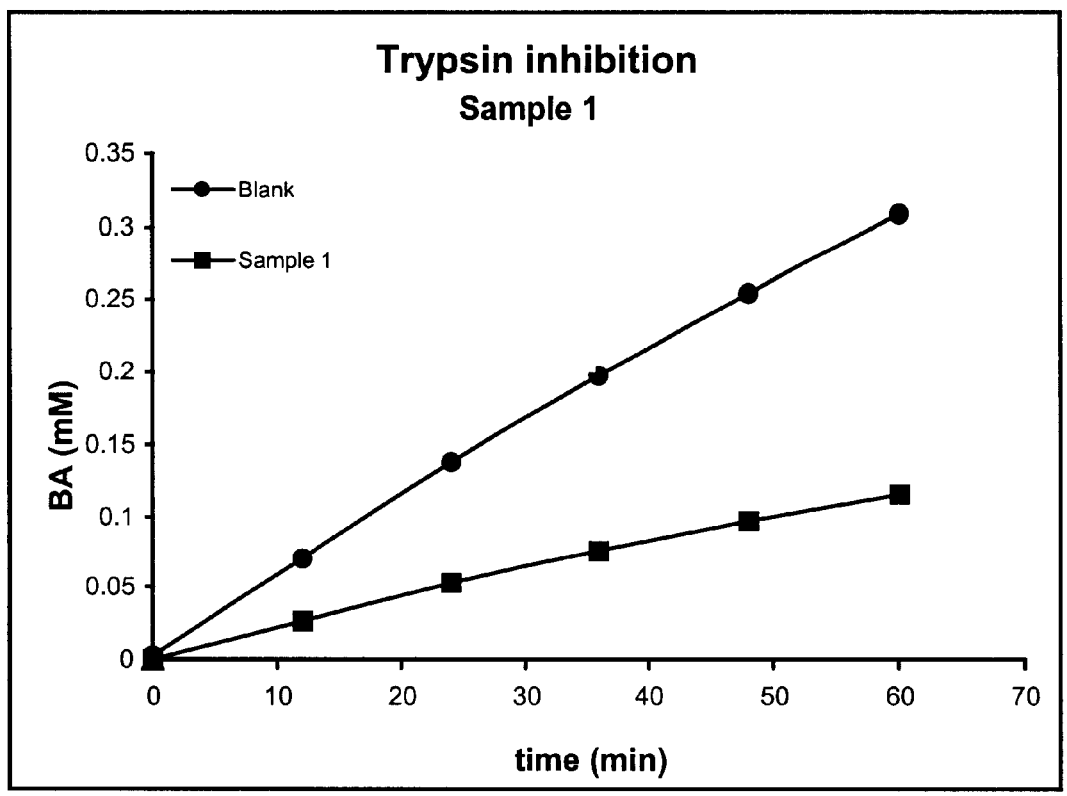
FIG. 3 is a graph showing trypsin inhibition.

Trypsin inhibition was measured as the evolution of N-alpha-benzoylarginine (BA) in mM over a period of 60 minutes. Results are shown in Table 1 and in FIG. 3. The Inhibition Factor (mean±sd) of Sample 1 was calculated to be 2.65±0.12.

TABLE 1

| | BA (mM) | | | | | |
|---|---|---|---|---|---|---|
| | 0 min. | 12 min. | 24 min. | 26 min. | 48 min. | 60 min. |
| Sample 1 | 0.0003 | 0.0264 | 0.0530 | 0.0752 | 0.0971 | 0.1153 |
| Sample 3 | 0.0024 | 0.0696 | 0.1384 | 0.1975 | 0.2551 | 0.3083 |

Sample 1 clearly demonstrates inhibition of the enzyme trypsin.

Example 2

Ex Vivo Bioadhesion

The in vitro bioadhesion strength of tablets, consisting of either 100 percent of Sample 1 or 100 percent of Sample 2, were measured using porcine mucosa as substrate. Adhesion force and the work of adhesion were determined. Results are shown in Table 2.

TABLE 2

| | Adhesion Force (N) | Work of Adhesion (mJ) |
|---|---|---|
| Sample 1 | 2.05 (±0.59) | 0.67 (±0.21) |
| Sample 2 | 1.22 (±0.4) | 0.29 (±0.09) |

It is clearly shown that Sample 1 prepared according to this invention has superior adhesion properties.

Example 3

Testosterone Delivery via a Buccal

Figure 4:
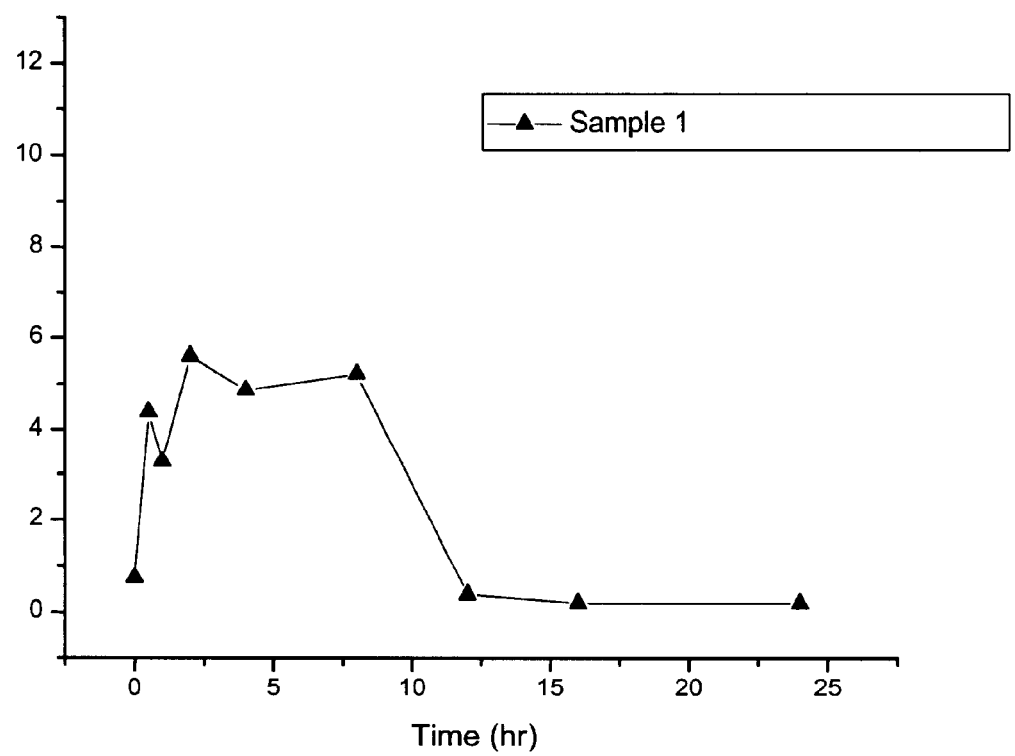
FIG. 4 is a graph showing delivery of testosterone.

Sample 1 was made into tablets and loaded with 60 mg of testosterone as a model drug. The tablets were administered to six neutered dogs. The tablets were applied in the mouth of the dogs on the mucosa above the upper canine. Plasma samples were taken over 24 hours and analyzed for testosterone. Table 3 and FIG. 4 show the averaged results from the six dogs.

TABLE 3

| | Plasma Testosterone (ng/ml) | | | | | | | | |
|---|---|---|---|---|---|---|---|---|---|
| | 0 | 0.5 hr. | 1 hr. | 2 hr. | 3 hr. | 8 hr. | 12 hr. | 16 hr. | 24 hr. |
| Sample 1 | 0.2 | 3.058 | 2.46 | 2.983 | 3.288 | 3.392 | 1.261 | 0.2 | 0.331 |

These results show that Sample 1 provides a constant release profile over 8 hours.

Example 4

Nasal Delivery of Peptides and Proteins

Figure 5:
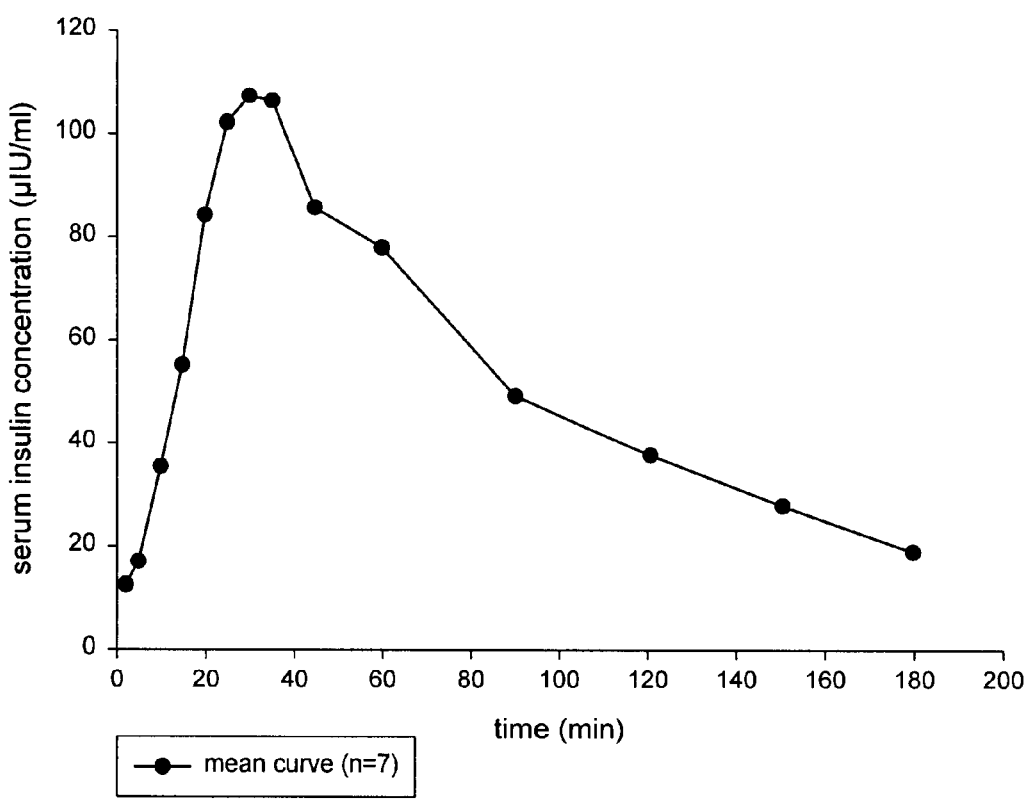
FIG. 5 is a graph showing delivery of insulin.

After neutralization of a dispersion of Sample 1 in distilled water, insulin was added in a ratio of 1 IU insulin per mg powder. This was lyophilized and the powder was then sieved through a sieve of 63 µm. 10 mg of the powder was given to rabbits per nostril. The serum insulin concentrations have been normalized to 5 IU insulin administered per kg of rabbit. Results are shown in Table 4 and in FIG. 5. The Nasal Absolute Bioavailability (%) (n=7) of Sample 1 was calculated to be 4.10±1.63.

TABLE 4

| Time (min) | Serum Insulin (µIU/ml) |
|---|---|
| 1.93 | 12.49 |
| 4.79 | 16.96 |
| 9.81 | 35.33 |
| 14.64 | 55.22 |
| 19.80 | 84.29 |
| 24.76 | 102.10 |
| 29.83 | 107.19 |
| 34.98 | 106.25 |
| 44.62 | 85.67 |
| 59.82 | 77.95 |
| 90.08 | 49.11 |

TABLE 4-continued

| Time (min) | Serum Insulin (µIU/ml) |
|---|---|
| 120.64 | 37.55 |
| 150.46 | 27.74 |
| 179.75 | 18.84 |

This clearly demonstrates the attainment of bioavailability via the nasal mucosa.

We claim:

1. A method of producing a bioadhesive composition comprising preparing a solution of at least one solvent and a polymer mixture wherein the polymer mixture comprises at least one poly(acrylic) acid and at least one starch having a molecular weight of at least 10,000 Daltons; drying the solution to form a solid; and heat treating the solid at a temperature and for a time sufficient to effect cross-linking and form a bioadhesive composition.

2. The method of claim 1 wherein the solid is heat treated at a temperature from about 60° C. to about 200° C.

3. The method of claim 1 wherein the poly(acrylic) acid is a modified poly(acrylic) acid.

4. The method of claim 1 wherein the solvent is water.

5. The method of claim 2 wherein the solid is heat treated at a temperature from about 80° C. to about 120° C.

6. The method of claim 1 wherein the poly(acrylic) acid has a weight average molecular weight of at least 1,000 Daltons.

7. The method of claim 1 wherein the poly(acrylic) acid is a cross-linked poly(acrylic) acid.

8. The method of claim 1 wherein the poly(acrylic) acid is cross-linked by a cross-linking material selected from the group consisting of allyl ethers of sucrose, pentaerythritol, and divinyl glycol.

9. The method of claim 1 wherein the poly(acrylic) acid is present in the polymer mixture in an amount of about 25 percent by weight to about 83 percent by weight.

10. The method of claim 1 wherein the starch is modified by etherification, esterification, acid hydrolysis, dextrinization, crosslinking, pregelatinization or enzyme treatment.

* * * * *